US006800086B2

(12) United States Patent
Strong

(10) Patent No.: US 6,800,086 B2
(45) Date of Patent: Oct. 5, 2004

(54) REDUCED FLUENCE RATE PDT

(75) Inventor: H. Andrew Strong, North Vancouver (CA)

(73) Assignee: QLT Inc., Vancouver (CA)

( * ) Notice: Subject to any disclaimer, the term of this patent is extended or adjusted under 35 U.S.C. 154(b) by 0 days.

(21) Appl. No.: 10/072,009

(22) Filed: Feb. 6, 2002

(65) Prior Publication Data

US 2002/0173832 A1 Nov. 21, 2002

Related U.S. Application Data

(60) Provisional application No. 60/266,960, filed on Feb. 6, 2001.

(51) Int. Cl.$^7$ .................................. A61F 9/007
(52) U.S. Cl. ....................... 607/88; 514/18; 128/898
(58) Field of Search ........................... 514/18; 607/88; 128/898

(56) References Cited

U.S. PATENT DOCUMENTS

| | | | |
|---|---|---|---|
| 5,756,541 A | 5/1998 | Strong et al. | 514/502 |
| 5,798,349 A | 8/1998 | Levy et al. | 514/185 |
| 5,910,510 A | 6/1999 | Strong et al. | 514/502 |
| 6,063,777 A | 5/2000 | Hikida et al. | 514/183 |
| 6,225,303 B1 | 5/2001 | Miller et al. | 514/185 |
| 6,270,749 B1 | 8/2001 | Blumenkranz et al. | 424/9.61 |
| 2001/0023247 A1 | 9/2001 | Gragoudas et al. | 514/185 |
| 2002/0025298 A1 | 2/2002 | Blumenkranz et al. | 604/20 |
| 2002/0040015 A1 | 4/2002 | Miller et al. | 514/185 |

FOREIGN PATENT DOCUMENTS

| | | |
|---|---|---|
| WO | WO 95/24930 | 9/1995 |
| WO | WO 01/35996 | 5/2001 |
| WO | WO 02/062386 | 8/2002 |

OTHER PUBLICATIONS

Bressler, N. "Submacular Surgery: Are Randomized Trials Necessary?" Arch Opthalmol. 113:1557–1560 (1995).
Foster, T.H. et al., "Analysis of Photochemical Oxygen Consumption Effects in Photodynamic Therapy" Optical Methods for Tumor Treatment and Detection 1645:104–14 (1992).
Henderson, B. et al., "Relationship of Tumor Hypoxia and Response to Photodynamic Treatment in an Experimental Mouse Tumor" Cancer Res. 47:3110–3114 (1987).
Henderson, B.W. et al., "Photofrin Photodynamic Therapy Can Significantly Deplete or Preserve Oxygenation in Human Basal Cell Carcinomas During Treatment, Depending on Fluence Rate" Cancer Research 60(3):525–529 (2000).
Klein, R. et al., "The Five–Year Incidence and Progression of Age–Related Maculopathy: The Beaver Dam Eye Study" Ophthalmol. 104(1):7–21 (1997).

Kreimer–Birmbaum, M. "Modified Porphyrins, Chlorins, Phthalocyanines, and Purpurins: Second Generation Photosensitizers for Photodynamic Therapy" Semin Hematol. 26:157–173 (1989).
Lear, J. et al., "Low Back Pain Associated with Streptokinase" Lancet 340:851 (1992).
Macular Photocoagulation Study Group. "Recurrent Choroidal Neovascularization After Argon Laser Photocoagulation for Neovascular Maculopathy" Arch Opthalmol. 104:503–512 (1986).
Macular Photocoagulation Study Group. "Argon Laser Photocoagulation for Neovascular Maculopathy. Three–Year Results from Randomized Clinical Trials" Arch Ophthalmol. 104:694–701 (1986).
Macular Photocoagulation Study Group. "Laser Photocoagulation of Subfoveal Neovascular Lesions of Age–Related Macular Degeneration. Updated Findings from Two Clinical Trials" Arch Opthalmol. 111:1200–1209 (1993).
Manyak, M.J., et al., "Photodynamic Therapy" J Clin Oncol 6:380–381 (1988).
Marcus, S. "Photodynamic Therapy of Human Cancer: Clinical Status, Potential and Needs" In Gomer C, ed. *Future Directions and Applications in Photodynamic Therapy* Berlingham: SPIE Press IS6:5–56 (1990).
Miller, J. et al., "Photodynamic Therapy with Verteporfin for Choroidal Neovascularization Caused by Age–Related Macular Degeneration" Arch. Ophthalmol. 117:1161–1173 (1999).
Moan, J. et al., "Photosensitizing Efficiencies, Tumor and Cellular Uptake of Different Photosensitizing Drugs Relevant for Photodynamic Therapy of Cancer" Photochem Photobiol. 46:713–721 (1987).
Roberts, W.G. et al., "In Vitro Photosensitization I. Cellular Uptake and Subcellular Localization of Mono–1–Aspartyl Chlorin e6, Chloro–ALuminum Sulfonated Phthalocyanine, and Photofrin II" Lasers Surg. Med. 9:90–101 (1989).
Roberts, W.G. et al., "Role of Neovasculature and Vascular Permeability on the Tumor Retention of Photodynamic Agents" Cancer Res. 52(4):924–930 (1992).

(List continued on next page.)

*Primary Examiner*—Roy D. Gibson
*Assistant Examiner*—Henry M Johnson, III
(74) *Attorney, Agent, or Firm*—Morrison & Foerster LLP

(57) ABSTRACT

The invention relates to the use of reduced fluence rate PDT to treat neovasculature, particularly choroidal neovasculature (CNV). Reduced fluence rate PDT decreases the likelihood of molecular oxygen being the limiting factor in the photodynamic reaction so that the concentration of either photons (light intensity) or photosensitizer in the target tissue controls the photodynamic reaction.

20 Claims, No Drawings

OTHER PUBLICATIONS

Sculier, J.P. et al., "Intravenous Infusion of High Doses of Liposomes Containing NSC 251635, A Water Insoluble Cytostatic Agent: A Pilot Study with Pharmacokinetic Data" J Clin Oncol 4:789–797 (1986).

Sitnik, T. et al., "The Effect of Fluence Rate on Tumor and Normal Tissue Responses to Photodynamic Therapy" Photochem. and Photobiol. 67(4):462–466 (1998).

Sitnik, T. et al., "Reduction of Tumour Oxygenation During and After Photodynamic Therapy In Vivo: Effects of Fluence Rate" British J. Cancer 77(9):1386–1394 (1998).

Treatment of Age–Related Macular Degeneration with Photodynamic Therapy (TAP) Study Group. "Photodynamic Therapy of Subfoveal Choroidal Neovascularization in Age–Related Macular Degeneration with VISUDYNE: One–Year Results of 2 Randomized Clinical Trials—TAP Report 1" Arch Ophthalmol. 117:1329–1345 (1999).

Tromberg, B. et al., "In Vivo Tumor Oxygen Tension Measurements for the Evaluation of the Efficiency of Photodynamic Therapy" Photochem. and Photobiol. 52(2):375–385 (1990).

REDUCED FLUENCE RATE PDT

This application claims benefit of priority from U.S. Provisional Patent Appl'n. No. 60/266,960 filed Feb. 6, 2001, which is hereby incorporated by reference as if fully set forth.

TECHNICAL FIELD

The invention relates to the use of reduced fluence rate photodynamic therapy (PDT) in the treatment of unwanted or undesirable neovasculature, especially that of the choroid. The invention is particularly advantageous in the treatment of ocular conditions and diseases.

BACKGROUND ART

Neovascularization occurs when either there is proliferation of blood vessels in tissues that would otherwise not contain or there is a growth of a different kind of blood vessel in a tissue. Unwanted neovascularization is associated with a number of disease conditions, such as that seen to occur with tumor growth or vision loss. One example of undesirable neovascularization in the eye is choroidal neovasculature (CNV) like that found in the "wet" form of age-related macular degeneration (AMD).

AMD causes severe, irreversible vision loss and is the leading cause of blindness in individuals older than 50 years in the Western World. Most patients have the non-neovascular ("dry") form, characterized by drusen and abnormalities of the retinal pigment epithelium (RPE). Eighty to ninety percent of the severe vision loss due to AMD, however, is attributable to the form characterized by CNV, also called "wet" AMD. In the United States, between 70,000 to 200,000 individuals over the age of 65 develop the neovascular form of AMD every year (Bressler, N. "Submacular surgery: Are randomized trials necessary?" *Arch Ophthalmol.* 1995;113;1557–1560; Klein, R. et al. "The five-year incidence and progression of age-related maculopathy: the Beaver Dam Eye Study." *Ophthalmol.* 1997;104 (1):7–21).

In CNV, the newly formed vessels have a tendency to leak blood and fluid, causing symptoms of scotoma and metamorphopsia (Macular Photocoagulation Study Group. "Argon laser photocoagulation for neovascular maculopathy. Three-year results from randomized clinical trials." *Arch Ophthalmol.* 1986;104:694–701). The new vessels are accompanied by proliferation of fibrous tissue (Macular Photocoagulation Study Group. "Laser photocoagulation of subfoveal neovascular lesions of age-related macular degeneration. Updated findings from two clinical trials." *Arch Ophthalmol.* 1993;111:1200–1209). This complex of new vessels and fibrous tissue can destroy photoreceptors within 3 to 24 months. At the same time that existing CNV is destroying retinal tissue where it has formed, the lesion can continue to grow throughout the macula, resulting in progressive, severe and irreversible vision loss. Without treatment, most affected eyes will have poor central vision (<20/200) within 2 years (Macular Photocoagulation Study Group. "Recurrent choroidal neovascularization after argon laser photocoagulation for neovascular maculopathy." *Arch Ophthalmol.* 1986;104:503–512). In addition, when one eye of an individual develops CNV, the fellow eye has about a 50% chance of developing a similar CNV lesion within 5 years (Treatment of Age-related Macular Degeneration With Photodynamic Therapy (TAP) Study Group. "Photodynamic therapy of subfoveal choroidal neovascularization in age-related macular degeneration with VISUDYNE: One-year results of 2 randomized clinical trials—TAP report 1." *Arch Ophthalmol.* 1999;117:1329–1345).

Photodynamic therapy (PDT) offers an approach to selectively destroy CNV without significant destruction of overlying retina tissue, possibly by occluding the new vessels within the CNV lesion. Photodynamic therapy is a two-step process consisting of an intravenous injection of a photosensitizer (light-activated drug) followed by light application (Marcus, S. "Photodynamic therapy of human cancer: clinical status, potential and needs." In: Gomer C, ed. Future Directions and Application In Photodynamic Therapy. Berlingham: SPIE Press. 1990;IS6:5–56; Manyak, M. J. et al. "Photodynamic therapy." *J Clin Oncol.* 1988;6:380–391; Roberts, W. G. et al. "Role of neovasculature and vascular permeability on the tumor retention of photodynamic agents." *Cancer Res.* 1992;52(4):924–930). The light sources most commonly used are non-thermal lasers or light emitting diodes (LEDs). Photosensitizers may preferentially accumulate in neovascular tissues, including the endothelial cells of choroidal neovascularization. In combination with localized light administration, this allows for selective treatment of the pathologic tissue (Kreimer-Birmbaum, M. "Modified porphyrins, chlorins, phthalocyanines, and purpurins: second generation photosensitizers for photodynamic therapy." *Semin Hematol.* 1989;26:157–173; Moan, J. et al. "Photosensitizing efficiencies, tumor and cellular uptake of different Photosensitizing drugs relevant for photodynamic therapy of cancer." *Photochem Photobiol.* 1987;46:713–721). After exposure to light at a wavelength of 689 nm, an energy transfer cascade is initiated, culminating in the formation of singlet oxygen which generates intracellular free radicals (Kreimer-Birmbaum, M., supra; Roberts, W. G. et al. "In vitro photosensitization I. Cellular uptake and subcellular localization of mono-1-aspartyl chlorin e6, chloro-aluminum sulfonated phthalocyanine, and Photofrin II." *Lasers Surg. Med.* 1989;9:90–101; Lear, J. et al. "Low back pain associated with streptokinase." *Lancet.* 1992;340:851). These free radicals can disrupt cellular structures such as the cell membrane, mitochondria, and lysosomal membranes (Sculier, J. P. et al. "Intravenous infusion of high doses of liposomes containing NSC 251635, a water insoluble cytostatic agent: A pilot study with pharmacokinetic data." *J Clin Oncol.* 1986;4:789–797).

Given the supply of oxygen available from the neovasculature, PDT has been particular effective at destroying CNV, presumably by occluding the neovasculature. Thus relatively high fluence rates of irradiation, such as approximately 600 mW/cm$^2$, have been used to activate the photosensitizer in PDT, with the limit on total light dose (in J/cm$^2$) being set by nonselective closure of retinal blood vessels and the associated vision loss (see Miller et al. Arch. Ophthalmol. 117:1161–1173 (1999)). The currently approved therapy uses 600 mW/cm$^2$ to deliver a total light dose of 50 J/cm$^2$. This therapy has also been found to enhance the visual acuity of treated subjects (see U.S. Pat. No. 5,756,541 for example).

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

DISCLOSURE OF THE INVENTION

The present invention relates to the use of photodynamic therapy (PDT) in the treatment of neovasculature and choroidal neovasculature (CNV) as a preferred embodiment. The photodynamic reaction is complex and generally requires a photosensitizer (PS), light, and molecular oxygen. Electromagnetic radiation of an appropriate excitatory wavelength activates the PS to result in the generation of an oxygen singlet free radical during PDT. In the presence of excess radiation during PDT, either molecular oxygen or PS may be rate-limiting in the production of free radicals. Under conditions where a PS is present at high concentrations, molecular oxygen is potentially the rate-limiting molecule. One possible example of such conditions is where PS accumulates preferentially in neovasculature and CNV.

The present invention is based in part on the unexpected discovery that molecular oxygen may be a limiting factor in PDT treatment of CNV. Where molecular oxygen is a limiting factor, irradiation beyond that necessary to activate the photosensitizer (PS) and generate singlet oxygen during PDT (or "excess irradiation") may be inefficient because the continued activation of PS is unable to generate any additional singlet oxygen. Moreover, the excess irradiation is likely to be counterproductive in the treatment of CNV by undermining the preferential accumulation of PS in the CNV. The extraneous irradiation, while being nonproductive at generating singlet oxygen in CNV, would continue to activate PS found in the surrounding normal choriocapillaris tissue where molecular oxygen is not a limiting factor the presence of a lower PS concentration. This continued activation of PS is likely aggravated by the higher oxygen tension found in normal choriocapillaris than in CNV and results in unwanted and/or undesirable damage to the surrounding normal tissue.

The present invention provides PDT with a lower amount of light per unit time (a lower fluence rate) to treat neovasculature and CNV. With reduced fluence rates, molecular oxygen concentrations around PS molecules in the CNV are less likely to become the rate-limiting factor in the photodynamic production of oxygen singlet free radicals. With a reduced fluence rate, the concentration of either photons (light intensity) or PS, rather than molecular oxygen, in the tissue would control the photodynamic reaction, resulting in better selectivity to the CNV, less damage to the normal choriocapillaris and possibly to the retinal pigment epithelium (RPE), and reduction of post-treatment hypoxia and resultant production of angiogenic factors. These effects would lead to improved visual outcome and a prolonged time period without leakage.

By minimizing the damage to the choriocapillaris and the response to that injury using a reduced fluence rate, the invention provides improve visual outcomes as well as lower rates of recurrence and CNV progression. Use of the invention is also expected to reduce the need for retreatments.

MODES OF CARRYING OUT THE INVENTION

The present invention is generally directed to the treatment of neovasculature, particularly CNV, by the efficient activation of a photo sensitizer (PS) in photodynamic therapy (PDT) under reduced fluence rate conditions. The reduced fluence rates of the invention decreases the likelihood of molecular oxygen levels in the CNV being the limiting factor in the photodynamic production of oxygen singlet free radicals. The invention provides improved control over PDT treatment of CNV by permitting either PS concentration or light intensity, rather than molecular oxygen, to limit the photodynamic reaction. By providing PS in excess, light intensity may be used as a very sensitive means for regulating the PDT process for the continued efficient generation of singlet oxygen free radicals. As will be appreciated by those skilled in the art, it is generally easier to regulate the level of PS concentration and/or light intensity than the level of molecular oxygen in a localized in vivo environment.

The invention also provides a more effective means for the efficient generation of singlet oxygen during PDT treatment of CNV. Given the original recognition that molecular oxygen levels may be the limiting factor in PDT used to treat CNV, the present invention provides an improved means for the treatment of CNV by permitting the more efficient generation of singlet oxygen (per amount of activating irradiation) as well as by permitting the continued production of singlet oxygen over prolonged periods without causing hypoxic conditions.

Throughout this disclosure, the shortened term "reduced fluence rate" is used to mean "reduced rate of applied light dose achieved by reduced fluence rate." Preferably, the reduced fluence rates of the invention result in better selectivity to the CNV as well as decrease closure of normal choriocapillaris and other unwanted or undesirable damage to normal tissue at or near the treated CNV. Because standard, higher, light fluence rates may lead to hypoxia, angiogenesis stimulation, further CNV growth, and possibly reductions of the duration of the therapeutic benefit, the reduced fluence rates of the invention avoid these possibilities by decreasing the likelihood of depleting molecular oxygen levels at the site of PDT. Without being bound by theory, it is hypothesized that a reduced light fluence rate will result in a more selective treatment benefit compared to controls using a higher fluence rate.

As used herein, "photodynamic productivity" or "photodynamic product" is meant to refer to the reaction product caused by the interaction of PS with electromagnetic radiation and molecular oxygen.

In the general approach that forms the subject matter of the invention, PDT with a reduced fluence rate is used to treat CNV in a subject afflicted or diagnosed therewith. PDT is basically conducted via conventional means, wherein the subject is administered a suitable PS compound in amount sufficient to provide an effective concentration of the PS at the site of the CNV. After a suitable time period to permit an effective concentration of the PS to accumulate, the region to be treated is irradiated (or illuminated or otherwise activated) with electromagnetic radiation containing one or more wavelengths which activate the PS. The resultant excitation of the PS likely causes the generation of singlet oxygen free radicals to cause deleterious effects on the immediately surrounding tissue. The ultimate result is closure of the CNV and enhancement of visual acuity in the subject.

In preferred embodiments of the invention, the subject to be treated is human, and the site of CNV is in the eye. In particularly preferred embodiments, the human subject is afflicted with the "wet" form of age-related macular degeneration (AMD). In other preferred embodiments of the invention, the irradiation step is with light containing wavelengths in the visible range.

Without being bound by theory, and offered for the purposes of improving the understanding of the invention rather than stipulating the mechanism underlying the invention, a hypothetical example of the stoichiometry of the photodynamic reaction with reduced fluence rate and standard fluence rate in the CNV and choriocapillaris is shown by the equation below. While the example uses Verteporfin as the PS, it will be understood that the example is generally applicable to any PS.

It is hypothesized that to obtain one unit of photodynamic productivity [P] (or photodynamic product or reaction) a stoichiometry of one unit of Verteporfin [V], one unit of molecular oxygen [$O_2$], and one unit of photons [λ] is required. It is also hypothesized that there is a greater selectivity of PS for the CNV relative to the choriocapillaris in a ratio of 5:4 and that there is a greater oxygen concentration in the choriocapillaris than in the CNV in a ratio of 4:3. These latter hypotheses are reasonable based on in vitro studies that have shown greater selectivity of PS for proliferating versus non-proliferating cells and suggestions from studies on AMD relative ischemia. The above also hypothesizes that there is a loss of photon concentration at the level of the choriocapillaris relative to the CNV because the choriocapillaris is at a slightly deeper level of the outer retina and there may be some attenuation of photons by the pigment in the RPE. It should be noted that while the example sets forth a one to one to one to one relationship between photodynamic productivity, PS, molecular oxygen, and light (photons), the relationship is offered for illustrative purposes only, and the actual relationship may vary. For the purposes of the example, it is only important that there is a relatively stable relationship between these four factors and that the relationship is the same in both the CNV and choriocapillaris.

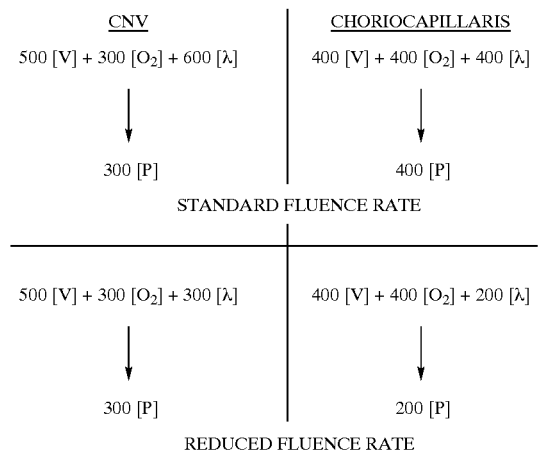

With the standard fluence rate in the example, molecular oxygen is limiting in the reaction stoichiometry, and because there is more molecular oxygen in the choriocapillaris there is a greater amount of photodynamic product or damage in that tissue (400 [P]) relative to that in the CNV (300 [P]).

With the reduced fluence rate in the example the photon concentration becomes limiting so there is a greater photodynamic product or reaction in the CNV (300 [P]) than in the choriocapillaris (200 [P]). Thus the photodynamic reaction in the CNV (300 [P]) is the same as that with the standard fluence rate so CNV closure would still occur, but the damage to the choriocapillaris is decreased by one-half. Thus a lower total light dose may have a more selective treatment effect on the CNV and less damage to the normal choriocapillaris.

The invention utilizes PDT methods which generally include the administration of a photosensitizer (PS) and irradiation with a wavelength of electromagnetic radiation capable of activating the PS. The invention also includes use of a PS in the preparation of a medicament for use in any of the methods described herein.

Preferred PSs of the invention are the green porphyrins, and preferred irradiation is with visible light. A particularly preferred PS is a lipid formulation of benzoporphyrin derivative monoacid ring A, which is also known as Verteporfin or BPD-MA. Following, or simultaneous with, delivery of the PS, irradiation may be performed by any radiation source. Examples of sources of visible light radiation include operating room lamps, halogen lamps, fluorescent lamps, laser light sources, and combinations thereof. Additional examples of light sources include light emitting diode (LED) panels or flexible light diffusers which may be wrapped around a blood vessel.

As used herein "electromagnetic radiation," unless otherwise indicated, is meant generally to refer to the visible light range of the electromagnetic spectrum, generally including wavelengths between 400 nm and 700 nm. The terms "visible light" and "visible light radiation" and variations thereof are meant to be encompassed within the scope of the term "electromagnetic radiation." In addition, this term may also be used herein to refer to electromagnetic radiation within the ultraviolet (including wavelengths below 400 nm) and infrared spectra (including wavelengths above 700 nm).

Preferably, radiation, such as 690 nm light in the case of BPD-MA use, is delivered. In one embodiment, the light is from a laser, such as that capable of stably delivering 689+/−3 nm, and delivered to the ocular environment. Examples of such techniques are discussed in Miller et al., supra.

Administration of the PS may be by delivery using any appropriate means including, but not limited to, systemic, local, or even direct application to the target tissue. Local delivery of the PS provides a high local concentration while reducing the likelihood of transient skin photosensitivity or other undesirable side effects that may follow systemic PS administration. Additional suitable PSs are of a wide variety, including, without limitation, porphyrin related compounds such as hematoporphyrin derivative, Photofrin® porfimer sodium, the green porphyrins such as the BPDs, purpurins, chlorins, fluorins, etiopurpurins, and the like as well as phthalocyanines, pheophorbides, deuteroporphyrins, texaphrins, and the like.

As used herein, the term "photosensitizer," "photosensitzer compound," "photosensitizing drug," "PS," and "photoactive agent" are used interchangeably. Any variation in meaning between these terms is not meant to depart form the gist and scope of the claimed invention.

Examples of these and other PSs for use in the present invention include, but are not limited to, angelicins, some biological macromolecules such as lipofuscin; photosystem II reaction centers; and D1-D2-cyt b-559 photosystem II reaction centers, chalcogenapyrillium dyes, chlorins, chlorophylls, coumarins, cyanines, ceratin DNA and related compounds such as adenosine; cytosine; 2'-deoxyguanosine-5'-monophosphate; deoxyribonucleic acid; guanine; 4-thiouridine; 2'-thymidine 5'-monophosphate; thymidylyl(3'–5')-2'-deoxyadenosine; thymidylyl(3'–5')-2'-deoxyguanosine; thymine; and uracil, certain drugs such as adriamycin; afloqualone; amodiaquine dihydrochloride; chloroquine diphosphate; chlorpromazine hydrochloride; daunomycin; daunomycinone; 5-iminodaunomycin; doxycycline; furosemide; gilvocarcin M; gilvocarcin V; hydroxychloroquine sulfate; lumidoxycycline; mefloquine hydrochloride; mequitazine; merbromin (mercurochrome); primaquine diphosphate; quinacrine dihydrochloride; quinine sulfate; and tetracycline hydrochloride, certain flavins and related compounds such as alloxazine; flavin mononucleotide; 3-hydroxyflavone; limichrome; limiflavin; 6-methylalloxazine; 7-methylalloxazine; 8-methylalloxazine; 9-methylalloxazine; 1-methyl limichrome; methyl-2-methoxybenzoate; 5-nitrosalicyclic acid; proflavine; and riboflavin, fullerenes, metalloporphyrins, metallophthalocyanines, methylene blue derivatives, naphthalimides, naphthalocyanines, certain natural compounds such as bis(4-hydroxy-3-methoxyphenyl)-1,6-heptadiene-3,5-dione; 4-(4-hydroxy-3-methoxyphenyl)-3-buten-2-one; N-formylkynurenine; kynurenic acid; kynurenine; 3-hydroxykynurenine; DL-3-hydroxykynurenine; sanguinarine; berberine; carmane; and 5,7,9(11),22-ergostatetraene-3 β-ol, nile blue derivatives, NSAIDs (nonsteroidal anti-inflammatory drugs), perylenequinones, phenols, pheophorbides, pheophytins, photosensitizer dimers and conjugates, phthalocyanines, porphycenes, porphyrins, psoralens, purpurins, quinones, retinoids, rhodamines, thiophenes, verdins, vitamins and xanthene dyes (Redmond and Gamlin, *Photochem. Photobiol.*, 70(4):391–475 (1999)).

Exemplary angelicins include 3-aceto-angelicin; angelicin; 3,4'-dimethyl angelicin; 4,4'-dimethyl angelicin; 4,5'-dimethyl angelicin; 6,4'-dimethyl angelicin; 6,4-dimethyl angelicin; 4,4',5'-trimethyl angelicin; 4,4',5'-trimethyl-1'-thioangelicin; 4,6,4'-trimethyl-1'-thioangelicin; 4,6,4'-trimethyl angelicin; 4,6,5'-trimethyl-1'-thioangelicin; 6,4,4'-trimethyl angelicin; 6,4',5'-trimethyl angelicin; 4,6,4',5'-tetramethyl-1'-thioangelicin; and 4,6,4',5'-tetramethyl angelicin.

Exemplary chalcogenapyrillium dyes include pyrilium perchlorate, 4,4'-(1,3-propenyl)-bis[2,6-di(1,1-dimethylethyl)]-; pyrilium perchlorate, 2,6-bis(1,1-dimethyl-ethyl)-4-[1-[2,6-bis(1,1-dimethyl-ethyl)selenopyran-4-ylidene]-3-propenyl-; pyrilium hexofluoro phosphate, 2,6-bis-(1,1-dimethyl-ethyl)-selenopyran-4-ylidene]-3-propenyl-; pyrilium hexofluoro phosphate, 2,6-bis(1,1-dimethyl-ethyl)-selenopyran-4-ylidene]-3-propenyl-; pyrilium perchlorate, 2,6-bis(1,1-dimethyl-ethyl)-4-[1-[2,6-bis(1,1-dimethyl-ethyl)telluropyran-4-ylidene]-3-propenyl-; pyrilium hexofluoro phosphate, 2,6-bis(1,1-dimethyl-ethyl)-4-[1-[2,6-bis(1,1-dimethyl-ethyl)telluropyran-4-ylidene]-3-propenyl-; pyrilium perchlorate, 2,6-bis(1,1-dimethyl-ethyl)-4-[1-[2,6-bis(1,1-dimethyl-ethyl)thiapyran-4-ylidene]-3-propenyl]-; selenopyrilium hexofluoro phosphate, 2,6-bis(1,1-dimethyl-ethyl)-4-[1-[2, 6-bis(1,1-dimethyl-ethyl)selenopyran-4-ylidene]-3-propenyl]-; selenopyrilium, 2,6-bis(1,1-dimethylethyl)-4-[1-[2,6-bis(1,1-dimethylethyl)selenopyran-4-ylidene]-3-propenyl]-; selenopyrilium percheorate, 2,6-bis(1,1-dimethyl-ethyl)-4-[1-[2,6-bis(1,1-dimethyl-ethyl)-4-[1-[2, 6-bis(1,1-dimethyl-ethyl)telluropyran-4-ylidene]-3-propenyl]-; selenopyrilium hexofluoro phosphate, 2,6-bis(1, 1-dimethyl-ethyl)-4-[1-[2,6-bis(1,1-dimethyl-ethyl)telluropyran-4-ylidene]-3-propenyl]-; selenopyrilium hexofluoro phosphate, 2,6-bis(1,1-dimethyl-ethyl)-4-[2-[2, 6-bis(1,1-dimethyl-ethyl)selenopyran-4-ylidene]-4-(2-butenyl)]-; selenopyrilium hexofluoro phosphate, 2,6-bis(1, 1-dimethyl-ethyl)-4-[2-[2,6-bis(1,1-dimethyl-ethyl) selenopyran-4-ylidene]-4-(2-pentenyl)]-; telluropyrilium tetrafluoroborate, 2,6-bis(1,1-dimethylethyl)-4-[1-[2,6-bis (1,1-dimethyl-ethyl)-telluropyran-4-ylidene]-3-propenyl]-; telluropyrilium hexofluoro phosphate, 2,6-bis(1,1-dimethyl-ethyl)-4-[1-[2,6-bis(1,1-dimethyl-ethyl)telluropyran-4-ylidene]-3-propenyl]-; telluropyrilium hexofluoro phosphate, 2,6-bis(1,1-dimethyl-ethyl)-4-[1-[2,6-bis(1,1-dimethyl-ethyl)telluropyran-4-ylidene]ethyl-; telluropyrilium hexofluoro phosphate, 2,6-bis(1,1-dimethyl-ethyl)-4-[1-[2,6-bis(1,1-dimethyl-ethyl)-telluropyran-4-ylidene] methyl-; thiopyrilium hexofluoro phosphate, 2,6-bis(1,1-dimethyl-ethyl)-4-[1-[2,6-bis(1,1-dimethyl-ethyl)thiopyran-4-ylidene]-3-propenyl]-; thiopyrilium hexofluoro phosphate, 2,6-bis(1,1-dimethyl-ethyl)-4-[1-[2,6-bis(1,1-dimethyl-ethyl)selenopyran-4-ylidene]-3-propenyl]-; and thiopyrilium hexofluoro phosphate, 2,6-bis(1,1-dimethyl-ethyl)-4-[1-[2,6-bis(1,1-dimethyl-ethyl)telluropyran-4-ylidene]-3-propenyl]-.

Exemplary chlorins dyes include 5-azachlorin dimethyl ester derivative; 5,10,15,20-tetrakis-(m-hydroxyphenyl) bacteriochlorin; benzoporphyrin derivative monoacid ring A; benzoporphyrin derivative monoacid ring-A; porphine-2,18-dipropanoic acid, 7-[2-dimethyl-amino)-2-oxoethyl]-8-ethylidene-7,8-dihydro-3,7,12,17-tetramethyl, dimethylester; porphine-2,18-dipropanoic acid, 7-[2-dimethyl-amino)-2-oxoethyl]-8-ethylidene-8-ethyl-7,8-dihydro-3,7, 12,17-tetramethyl, dimethylester Z; porphine-2,18-dipropanoic acid, 7-[2-dimethyl-amino)-2-oxoethyl]-8-ethylidene-8-ethyl-7,8-dihydro-3,7,12,17-tetramethyl, dimethylester Z ECHL; porphine-2,18-dipropanoic acid, 7-[2-dimethyl-amino)-2-oxoethyl]-8-ethylidene-8-n-heptyl-7,8-dihydro-3,7,12,17-tetramethyl, dimethylester Z; tin (II) porphine-2,18-dipropanoic acid, 7-[2-(dimethylamino-2-oxoethyl]-8-ethylidene-8-n-heptyl-7,8-dihydro-3,7,12,17-tetramethyl, dimethylester Z; chlorin $e_6$; chlorin $e_6$ dimethyl ester; chlorin $e_6$ $k_3$; chlorin $e_6$ monomethyl ester; chlorin $e_6$ $Na_3$; chlorin $p_6$; chlorin $p_6$-trimethylester; chlorin derivative zinc (II) porphine-2,18-dipropanoic acid, 7-[2-(dimethylamino)-2-oxoethyl]-8-ethylidene-8-n-heptyl-7,8-dihydro-3,7,12,17-tetramethyl, dimethylester Z; $13^1$-deoxy-20-formyl-vic-dihydroxy-bacteriochlorin di-tert-butyl aspartate; $13^1$-deoxy-20-formyl-4-keto-bacteriochlorin di-tert-butyl aspartate; di-L-aspartyl chlorin $e_6$; mesochlorin; 5,10,15,20-tetrakis-(m-hydroxyphenyl) chlorin; meta-(tetrahydroxyphenyl)chlorin; methyl-$13^1$-deoxy-20-formyl-4-keto-bacteriochlorin; mono-L-aspartyl chlorin $e_6$; photoprotoporphyrin IX dimethyl ester; phycocyanobilin dimethyl ester; protochlorophyllide a; tin (IV) chlorin $e_6$; tin chlorin $e_6$; tin L-aspartyl chlorin $e_6$; tin octaethyl-benzochlorin; tin (IV) chlorin; zinc chlorin $e_6$; and zinc L-aspartyl chlorin $e_6$.

Exemplary chlorophylls dyes include chlorophyll a; chlorophyll b; oil soluble chlorophyll; bacteriochlorophyll a; bacteriochlorophyll b; bacteriochlorophyll c; bacteriochlorophyll d; protochlorophyll; protochlorophyll a; amphiphilic chlorophyll derivative 1; and amphiphilic chlorophyll derivative 2.

Exemplary coumarins include 3-benzoyl-7-methoxycoumarin; 7-diethylamino-3-thenoylcoumarin; 5,7-dimethoxy-3-(1-naphthoyl)coumarin; 6-methylcoumarin; 2H-selenolo[3,2-g] [1] benzopyran-2-one; 2H-selenolo[3,2-g] [1] benzothiopyran-2-one; 7H-selenolo[3,2-g] [1] benzoseleno-pyran-7-one; 7H-selenopyrano[3,2-f] [1] benzofuran-7-one; 7H-selenopyrano[3,2-f] [1] benzo-thiophene-7-one; 2H-thienol[3,2-g] [1] benzopyran-2-one; 7H-thienol[3,2-g] [1] benzothiopyran-7-one; 7H-thiopyrano [3,2-f] [1] benzofuran-7-one; coal tar mixture; khellin; RG 708; RG277; and visnagin.

Exemplary cyanines include benzoselenazole dye; benzoxazole dye; 1,1'-diethyloxacarbocyanine; 1,1'-diethyloxadicarbocyanine; 1,1'-diethylthiacarbocyanine; 3,3'-dialkylthiacarbocyanines (n=2–18); 3,3'-diethylthiacarbocyanine iodide; 3,3'- dihexylselenacarbocyanine; kryptocyanine; MC540 benzoxazole derivative; MC540 quinoline derivative; merocyanine 540; and meso-ethyl, 3,3'-dihexylselenacarbocyanine.

Exemplary fullerenes include $C_{60}$; $C_{70}$; $C_{76}$; dihydrofullerene; 1,9-(4-hydroxy-cyclohexano)-buckminsterfullerene; [1-methyl-succinate-4-methyl-cyclohexadiene-2,3]-buckminster-fullerene; and tetrahydro fullerene.

Exemplary metalloporphyrins include cadmium (II) chlorotexaphyrin nitrate; cadmium (II) meso-diphenyl tetrabenzoporphyrin; cadmium meso-tetra-(4-N-methylpyridyl)-porphine; cadmium (II) texaphyrin; cadmium (II) texaphyrin nitrate; cobalt meso-tetra-(4-N-methylpyridyl)-porphine; cobalt (II) meso(4-sulfonatophenyl)-porphine; copper hematoporphyrin; copper meso-tetra-(4-N-methylpyridyl)-porphine; copper (II) meso(4-sulfonatophenyl)-porphine; Europium (M) dimethyltexaphyrin dihydroxide; gallium tetraphenylporphyrin; iron meso-tetra(4-N-methylpyridyl)-porphine; lutetium (III) tetra(N-methyl-3-pyridyl)-porphyrin chloride; magnesium (II) meso-diphenyl tetrabenzoporphyrin; magnesium tetrabenzoporphyrin; magnesium tetraphenylporphyrin; magnesium (II) meso(4-sulfonatophenyl)-porphine; magnesium (II) texaphyrin hydroxide metalloporphyrin; magnesium meso-tetra-(4-N-methylpyridyl)-porphine; manganese meso-tetra-(4-N-methylpyridyl)-porphine; nickel meso-tetra(4-N-methylpyridyl)-porphine; nickel (II) meso-tetra(4-sulfonatophenyl)-porphine; palladium (II) meso-tetra-(4-N-methylpyridyl)-porphine; palladium meso-tetra-(4-N-methylpyridyl)-porphine; palladium tetraphenylporphyrin; palladium (II) meso(4-sulfonatophenyl)-porphine; platinum (II) meso(4-sulfonatophenyl)-porphine; samarium (II) dimethyltexaphyrin dihydroxide; silver (II) meso(4-sulfonatophenyl)-porphine; tin (IV) protoporphyrin; tin meso-tetra-(4-N-methylpyridyl)-porphine; tin meso-tetra(4-sulfonatophenyl)-porphine; tin (IV) tetrakis(4-sulfonatophenyl)porphyrin dichloride; zinc (II) 15-aza-3,7,12,18-tetramethyl-porphyrinato-13,17-diyl-dipropionic acid-dimethylester; zinc (II) chlorotexaphyrin chloride; zinc coproporphyrin III; zinc (II) 2,11,20,30-tetra-(1,1-dimethyl-ethyl)tetranaphtho(2,3-b:2',3'-g:2"3"-1:2'",3'"-q) porphyrazine; zinc (II) 2-(3-pyridyloxy)benzo[b]-10,19,28-tri(1,1-dimethylethyl)trinaphtho[2',3'-g:2"3"1::2'",3'"-q]porphyrazine; zinc (II) 2,18-bis-(3-pyridyloxy)dibenzo[b,1]-10,26-di(1,1-dimethyl-ethyl)dinaphtho[2',3'-g:2'",3'"-q]porphyrazine; zinc (II) 2,9-bis-(3-pyridyloxy)dibenzo[b,g]-17,26-di(1,1-dimethyl-ethyl)dinaphtho[2",3"-1:2'",3'"-q]porphyrazine; zinc (II) 2,9,16-tris-(3-pyridyloxy) tribenzo[b,g,1]-24=(1,1-dimethyl-ethyl)naphtho[2'",3'"-q]porphyrazine; zinc (II) 2,3-bis-(3-pyridyloxy)benzo[b]-10,19,28-tri(1.1-dimethyl-ethyl)trinaphtho[2',3'-g:2",3"1:2'", 3'"-q]porphyrazine; zinc (II) 2,3,18,19-tetrakis-(3-pyridyloxy)dibenzo[b,1]-10,26-di(1,1-dimethyl-ethyl)trinaphtho[2',3'-g:2'",3'"-q]porphyrazine; zinc (II) 2,3,9,10-tetrakis-(3-pyridyloxy)dibenzo[b,g]-17,26-di(1,1-dimethyl-ethyl)dinaphtho[2",3"-1:2'",3'"-q]porphyrazine; zinc (II) 2,3,9,10,16,17-hexakis-(3-pyridyloxy)tribenzo[b,g,1]-24-(1,1-dimethyl-ethyl)naphtho[2'",3'"-q]porphyrazine; zinc (II) 2-(3-N-methyl)pyridyloxy)benzo[b]-10,19,28-tri(1,1-dimethyl-ethyl)trinaphtho[2',3'-g:2",3"1:2'",3'"-q] porphyrazine monoiodide; zinc (II) 2,18-bis-(3-(N-methyl) pyridyloxy)dibenzo[b,1]-10,26-di(1,1-dimethylethyl) dinaphtho[2',3'-g:2'",3'"-q]porphyrazine diiodide; zinc (II) 2,9-bis-(3-(N-methyl)pyridyloxy)dibenzo[b,g]-17,26-di(1,1-dimethylethyl)dinaphtho[2",3"-1:2'",3'"-q]porphyrazine diiodide; zinc (II) 2,9,16-tris-(3-(N-methyl-pyridyloxy) tribenzo[b,g,1]-24-(1,1-dimethylethyl)naphtho[2'",3'"-q] porphyrazine triiodide; zinc (II) 2,3-bis-(3-(N-methyl) pyridyloxy)benzo[b]-10,19,28-tri(1,1-dimethylethyl) trinaphtho[2',3'-g:2",3"-1:2'",3'"-q]porphyrazine diiodide; zinc (II) 2,3,18,19-tetrakis-(3-(N-methyl)pyridyloxy) dibenzo[b,1]-10,26-di(1,1-dimethyl)dinaphtho[2',3'-g:2'", 3'"-q]porphyrazine tetraiodide; zinc (II) 2,3,9,10-tetrakis-(3-(N-methyl)pyridyloxy)dibenzo[g,g]-17,26-di(1,1-dimethylethyl)dinaphtho[2",3"-1:2'",3'"-q]porphyrazine tetraiodide; zinc (II) 2,3,9,10,16,17-hexakis-(3-(N-methyl) pyridyloxy)tribenzo[b,g,1]-24-(1,1-dimethylethyl)naphtho [2'",3'"-q]porphyrazine hexaiodide; zinc (II) meso-diphenyl tetrabenzoporphyrin; zinc (II) meso-triphenyl tetrabenzoporphyrin; zinc (II) meso-tetrakis(2,6-dichloro-3-sulfonatophenyl)porphyrin; zinc (II) meso-tetra-(4-N-methylpyridyl)-porphine; zinc (II) 5,10,15,20-meso-tetra(4-octyl-phenylpropynyl)-porphine; zinc porphyrin c; zinc protoporphyrin; zinc protoporphyrin IX; zinc (II) meso-triphenyl-tetrabenzoporphyrin; zinc tetrabenzoporphyrin; zinc (II) tetrabenzoporphyrin; zinc tetranaphthaloporphyrin; zinc tetraphenylporphyrin; zinc (II) 5,10,15,20-tetraphenylporphyrin; zinc (II) meso (4-sulfonatophenyl)-porphine; and zinc (II) texaphyrin chloride.

Exemplary metallophthalocyanines include aluminum mono-(6-carboxy-pentyl-amino-sulfonyl)-trisulfophthalocyanine; aluminum di-(6-carboxy-pentyl-aminosulfonyl)-trisulfophthalocyanine; aluminum (III) octa-n-butoxy phthalocyanine; aluminum phthalocyanine; aluminum (III) phthalocyanine disulfonate; aluminum phthalocyanine disulfonate; aluminum phthalocyanine disulfonate (cis isomer); aluminum phthalocyanine disulfonate (clinical prep.); aluminum phthalocyanine phthalimidomethyl sulfonate; aluminum phthalocyanine sulfonate; aluminum phthalocyanine trisulfonate; aluminum (III) phthalocyanine trisulfonate; aluminum (III) phthalocyanine tetrasulfonate; aluminum phthalocyanine tetrasulfonate; chloroaluminum phthalocyanine; chloro aluminum phthalocyanine sulfonate; chloroaluminum phthalocyanine disulfonate; chloroaluminum phthalocyanine tetrasulfonate; chloroaluminum-t-butyl-phthalocyanine; cobalt phthalocyanine sulfonate; copper phthalocyanine sulfonate; copper (II) tetra-carboxy-phthalocyanine; copper (II)-phthalocyanine; copper t-butyl-phthalocyanine; copper phthalocyanine sulfonate; copper (II) tetrakis-[methylene-thio[(dimethyl-amino)methylidyne]]phthalocyanine tetrachloride; dichlorosilicon phthalocyanine; gallium (III) octa-n-butoxy phthalocyanine; gallium (II) phthalocyanine disulfonate; gallium phthalocyanine disulfonate; gallium phthalocyanine tetrasulfonate-chloride; gallium (II) phthalocyanine tetrasulfonate; gallium phthalocyanine trisulfonate-chloride; gallium (II) phthalocyanine trisulfonate; $GaPcS_1tBu_3$; $GaPcS_2tBu_2$; $GaPcS_3tBu_1$; germanium (IV) octa-n-butoxy phthalocyanine; germanium phthalocyanine derivative; silicon phthalocyanine derivative; germanium (IV) phthalocyanine octakis-alkoxy-derivatives; iron phthalocyanine sulfonate; lead (II) 2,3,9,10,16,17,23,24-octakis(3,6-dioxaheptyloxy) phthalocyanine; magnesium t-butyl-phthalocyanine; nickel (II) 2,3,9,10,16,17,23,24-octakis(3,6-dioxaheptyloxy) phthalocyanine; palladium (II) octa-n-butoxy phthalocyanine; palladium (II) tetra(t-butyl)-phthalocyanine; (diol) (t-butyl)$_3$-phthalocyanato palladium (II); ruthenium(II) dipotassium[bis(triphenyl-phosphine-monosulphonate) phthalocyanine; silicon phthalocyanine bis(tri-n-hexyl-siloxy)-; silicon phthalocyanine bis(tri-phenyl-siloxy)-; $HOSiPcOSi(CH_3)_2(CH_2)_3N(CH_3)_2$; $HOSiPcOSi(CH_3)_2(CH_2)_3N(CH_2CH_3)_2$; $SiPc[OSi(CH_3)_2(CH_2)_3N(CH_3)_2]_2$; $SiPc[OSi(CH_3)_2(CH_2)_3N(CH_2CH_3)(CH_2)_2N(CH_3)_2]_2$; tin (IV) octa-n-butoxy phthalocyanine; vanadium phthalocyanine sulfonate; zinc (II) octa-n-butoxy phthalocyanine; zinc (II) 2,3,9,10,16,17,23,24-octakis(2-ethoxy-ethoxy) phthalocyanine; zinc (II) 2,3,9,10,16,17,23,24-octakis(3,6-dioxaheptyloxy) phthalocyanine; zinc (II) 1,4,8,11,15,18,22,25-octa-n-butoxy-phthalocyanine; zn(II)-phthalocyanine-octabutoxy; zn(II)-phthalocyanine; zinc phthalocyanine; zinc (II) phthalocyanine; zinc phthalocyanine and perdeuterated zinc phthalocyanine; zinc (II) phthalocyanine disulfonate; zinc phthalocyanine disulfonate; zinc phthalocyanine sulfonate; zinc phthalocyanine tetrabromo-; zinc (II) phthalocyanine tetra-t-butyl-; zinc (II) phthalocyanine tetra-(t-butyl)-; zinc phthalocyanine tetracarboxy-; zinc phthalocyanine tetrachloro-; zinc phthalocyanine tetrahydroxyl; zinc phthalocyanine tetraiodo-; zinc ((I) tetrakis-(1,1-dimethyl-2-phthalimido)ethyl phthalocyanine; zinc (II) tetrakis-(1,1-dimethyl-2-amino)-ethyl-phthalocyanine; zinc (II) phthalocyanine tetrakis(1,1-dimethyl-2-trimethyl ammonium)ethyl tetraiodide; zinc phthalocyanine tetrasulphonate; zinc phthalocyanine tetrasulfonate; zinc (II) phthalocyanine tetrasulfonate; zinc (II) phthalocyanine trisulfonate; zinc phthalocyanine trisulfonate; zinc (II) (t-butyl)$_3$-phthalocyanine diol; zinc tetradibenzobarreleno-octabutoxy-phthalocyanine; zinc (II) 2,9,16,23,-tetrakis-(3-(N-methyl)pyridyloxy)phthalocyanine tetraiodide; and zinc (II) 2,3,9,10,16,17,23,24-octakis-(3-(N-methyl)pyridyloxy) phthalocyanine complex octaiodide; and zinc (II) 2,3,9,10,16,17,23,24-octakis-(3-pyridyloxy)phthalocyanine.

Exemplary methylene blue derivatives include 1-methyl methylene blue; 1,9-dimethyl methylene blue; methylene blue; methylene blue (16 μM); methylene blue (14 μM; methylene violet; bromomethylene violet; 4-iodomethylene violet; 1,9-dimethyl-3-dimethyl-amino-7-diethyl-amino-phenothiazine; and 1,9-dimethyl-3-diethylamino-7-dibutyl-amino-phenothiazine.

Exemplary naphthalimides blue derivatives include N,N'-bis-(hydroperoxy-2-methoxyethyl)-1,4,5,8-naphthaldiimide; N-(hydroperoxy-2-methoxyethyl)-1,8-naphthalimide; 1,8-naphthalimide; N,N'-bis(2,2-dimethoxyethyl)-1,4,5,8-naphthaldiimide; and N,N'-bis(2,2-dimethylpropyl)-1,4,5,8-naphthaldiimide.

Exemplary naphthalocyanines include aluminum t-butyl-chloronaphthalocyanine; silicon bis(dimethyloctadecylsiloxy) 2,3-naphthalocyanine; silicon bis(dimethyloctadecylsiloxy)naphthalocyanine; silicon bis(dimethylthexylsiloxy) 2,3-naphthalocyanine; silicon bis(dimethylthexylsiloxy)naphthalocyanine; silicon bis(t-butyldimethylsiloxy) 2,3-naphthalocyanine; silicon bis(tert-butyldimethylsiloxy)naphthalocyanine; silicon bis(tri-n-hexylsiloxy) 2,3-naphthalocyanine; silicon bis(tri-n-hexylsiloxy)naphthalocyanine; silicon naphthalocyanine; t-butylnaphthalocyanine; zinc (II) naphthalocyanine; zinc (II) tetraacetyl-amidonaphthalocyanine; zinc (II) tetraaminonaphthalocyanine; zinc (II) tetrabenzamidonaphthalocyanine; zinc (II) tetrahexylamidonaphthalocyanine; zinc (II) tetramethoxy-benzamidonaphthalocyanine; zinc (II) tetramethoxynaphthalocyanine; zinc naphthalocyanine tetrasulfonate; and zinc (II) tetradodecylamidonaphthalocyanine.

Exemplary nile blue derivatives include benzo[a]phenothiazinium, 5-amino-9-diethylamino-; benzo[a]phenothiazinium, 5-amino-9-diethylamino-6-iodo-; benzo[a]phenothiazinium, 5-benzylamino-9-diethylamino-; benzo[a]phenoxazinium, 5-amino-6,8-dibromo-9-ethylamino-; benzo[a]phenoxazinium, 5-amino-6,8-diiodo-9-ethylamino-; benzo[a]phenoxazinium, 5-amino-6-bromo-9-diethylamino-; benzo[a]phenoxazinium, 5-amino-9-diethylamino-(nile blue A); benzo[a]phenoxazinium, 5-amino-9-diethylamino-2,6-diiodo-; benzo[a]phenoxazinium, 5-amino-9-diethylamino-2,-iodo; benzo[a] phenoxazinium, 5-amino-9-diethylamino-6-iodo-; benzo[a]phenoxazinium, 5-benzylamino-9-diethylamino-(nile blue 2B); 5-ethylamino-9-diethylamino-benzo[a]phenoselenazinium chloride; 5-ethylamino-9-diethyl-aminobenzo[a]phenothiazinium chloride; and 5-ethylamino-9-diethyl-aminobenzo[a]phenoxazinium chloride.

Exemplary NSAIDs (nonsteroidal anti-inflammatory drugs) include benoxaprofen; carprofen; carprofen dechlorinated (2-(2-carbazolyl) propionic acid); carprofen (3-chlorocarbazole); chlorobenoxaprofen; 2,4-dichlorobenoxaprofen; cinoxacin; ciprofloxacin; decarboxy-ketoprofen; decarboxy-suprofen; decarboxy-benoxaprofen; decarboxy-tiaprofenic acid; enoxacin; fleroxacin; fleroxacin-N-oxide; flumequine; indoprofen; ketoprofen; lomelfloxacin; 2-methyl-4-oxo-2H-1,2-benzothiazine-1,1-dioxide; N-demethyl fleroxacin; nabumetone; nalidixic acid; naproxen; norfloxacin; ofloxacin; pefloxacin; pipemidic acid; piroxicam; suprofen; and tiaprofenic acid.

Exemplary perylenequinones include hypericins such as hypericin; hypericin monobasic sodium salt; di-aluminum hypericin; di-copper hypericin; gadolinium hypericin; terbium hypericin, hypocrellins such as acetoxy hypocrellin A; acetoxy hypocrellin B; acetoxy iso-hypocrellin A; acetoxy iso-hypocrellin B; 3,10-bis[2-(2-aminoethylamino)ethanol] hypocrellin B; 3,10-bis[2-(2-aminoethoxy)ethanol] hypocrellin B; 3,10-bis[4-(2-aminoethyl)morpholine] hypocrellin B; n-butylaminated hypocrellin B; 3,10-bis(butylamine) hypocrellin B; 4,9-bis(butylamine) hypocrellin B; carboxylic acid hypocrellin B; cystamine-hypocrellin B; 5-chloro hypocrellin A or 8-chloro hypocrellin A; 5-chloro hypocrellin B or 8-chloro hypocrellin B; 8-chloro hypocrellin B; 8-chloro hypocrellin A or 5-chloro hypocrellin A; 8-chloro hypocrellin B or 5-chloro hypocrellin B; deacetylated aldehyde hypocrellin B; deacetylated hypocrellin B; deacetylated hypocrellin A; deacylated, aldehyde hypocrellin B; demethylated hypocrellin B; 5,8-dibromo hypocrellin A; 5,8-dibromo hypocrellin B; 5,8-dibromo iso-hypocrellin B; 5,8-dibromo[1,12-CBr=CMeCBr(COMe)] hypocrellinB; 5,8-dibromo[1,12-CHBrC(=CH$_2$)CBr(COMe)] hypocrellin B; 5,8-dibromo[1-CH$_2$COMe, 12-COCOCH$_2$Br—] hypocrellin B; 5,8-dichloro hypocrellin A; 5,8-dichloro hypocrellin B; 5,8-dichlorodeacytylated hypocrellin B; 5,8-diiodo hypocrellin A; 5,8-diiodo hypocrellin B; 5,8-diiodo [1,12-CH=CMeCH(COCH$_2$I$_2$)—] hypocrellin B; 5,8-diiodo[1,12-CH$_2$C(CH$_2$I)=C(COMe)—] hypocrellin B; 2-(N,N-diethylamino) ethylaminated hypocrellin B; 3,10-bis[2-(N,N-diethylamino)-ethylamine]hypocrellin B; 4,9-bis[2-(N,N-diethyl-amino)-ethylamine] iso-hypocrellin B; dihydro-1,4-thiazine carboxylic acid hypocrellin B; dihydro-1,4-thiazine hypocrellin B; 2-(N,N-dimethylamino) propylamine hypocrellin B; dimethyl-1,3,5,8,10,12-hexamethoxy-4,9-perylenequinone-6,7-diacetate; dimethyl-5,8-dihydroxy-1,3,10,13-tetramethoxy-4,9-perylenequinone-6,7-diacetate; 2,11-dione hypocrellin A; ethanolamine hypocrellin B; ethanolamine iso-hypocrellin B; ethylenediamine hypocrellin B; 11-hydroxy hypocrellin B or 2-hydroxy hypocrellin B; hypocrellin A; hypocrellin B; 5-iodo[1,12-CH$_2$C(CH$_2$I)=C(COMe)—] hypocrellin B; 8-iodo[1,12-CH$_2$C(CH$_2$I)=C(COMe)—] hypocrellin B; 9-methylamino iso-hypocrellin B; 3,10-bis[2-(N,N-methylamino)propylamine]hypocrellin B; 4,9-bis (methylamine iso-hypocrellin B; 14-methylamine iso-hypocrellin B; 4-methylamine iso-hypocrellin B; methoxy hypocrellin A; methoxy hypocrellin B; methoxy iso-hypocrellin A; methoxy iso-hypocrellin B; methylamine hypocrellin B; 2-morpholino ethylaminated hypocrellin B; pentaacetoxy hypocrellin A; PQP derivative; tetraacetoxy hypocrellin B; 5,8,15-tribromo hypocrellin B; calphostin C; Cercosporins such as acetoxy cercosporin; acetoxy iso-cercosporin; aminocercosporin; cercosporin; cercosporin+iso-cercosporin (1/1 molar); diaminocercosporin; dimethyl-cercosporin; 5,8-dithiophenol cercosporin; iso-cercosporin; methoxycercosporin; methoxy iso-cercosporin; methylcercosporin; noranhydrocercosporin; elsinochrome A; elsinochrome B; phleichrome; and rubellin A.

Exemplary phenols include 2-benzylphenol; 2,2'-dihydroxybiphenyl; 2,5-dihydroxybiphenyl; 2-hydroxybiphenyl; 2-methoxybiphenyl; and 4-hydroxybiphenyl.

Exemplary pheophorbides include pheophorbide a; methyl $13^1$-deoxy-20-formyl-7,8-vic-dihydro-bacterio-meso-pheophorbide a; methyl-2-(1-dodecyloxyethyl)-2-devinyl-pyropheophorbide a; methyl-2-(1-heptyl-oxyethyl)-2-devinyl-pyropheophorbide a; methyl-2-(1-hexyl-oxyethyl)-2-devinyl-pyropheophorbide a; methyl-2-(1-methoxy-ethyl)-2-devinyl-pyropheophorbide a; methyl-2-(1-pentyl-oxyethyl)-2-devinyl-pyropheophorbide a; magnesium methyl bacteriopheophorbide d; methyl-bacteriopheophorbide d; and pheophorbide.

Exemplary pheophytins include bacteriopheophytin a; bacteriopheophytin b; bacteriopheophytin c; bacteriopheophytin d; 10-hydroxy pheophytin a; pheophytin; pheophytin a; and protopheophytin.

Exemplary photosensitizer dimers and conjugates include aluminum mono-(6-carboxy-pentyl-amino-sulfonyl)-trisulfophthalocyanine bovine serum albumin conjugate; dihematoporphyrin ether (ester); dihematoporphyrin ether; dihematoporphyrin ether (ester)-chlorin; hematoporphyrin-chlorin ester; hematoporphyrin-low density lipoprotein conjugate; hematoporphyrin-high density lipoprotein conjugate; porphine-2,7,18-tripropanoic acid, 13,13'-(1,3-propanediyl) bis[3,8,12,17-tetramethyl]-; porphine-2,7,18-tripropanoic acid, 13,13'-(1,11-undecanediyl)bis[3,8,12,17-tetramethyl]-; porphine-2,7,18-tripropanoic acid, 13,13'-(1,6-hexanediyl) bis[3,8,12,17-tetramethyl]-; SnCe6-MAb conjugate 1.7:1; SnCe6-MAb conjugate 1.7:1; SnCe6-MAb conjugate 6.8:1; SnCe6-MAb conjugate 11.2:1; SnCe6-MAb conjugate 18.9:1; SnCe6-dextran conjugate 0.9:1; SnCe6-dextran conjugate 3.5:1; SnCe6-dextran conjugate 5.5:1; SnCe6-dextran conjugate 9.9:1; α-terthienyl-bovine serum albumin conjugate (12:1); α-terthienyl-bovine serum albumin conjugate (4:1); and tetraphenylporphine linked to 7-chloroquinoline.

Exemplary phthalocyanines include (diol) (t-butyl)$_3$-phthalocyanine; (t-butyl)$_4$-phthalocyanine; cis-octabutoxy-dibenzo-dinaphtho-porphyrazine; trans-octabutoxy-dibenzo-dinaphtho-porphyrazine; 2,3,9,10,16,17,23,24-octakis2-ethoxyethoxy) phthalocyanine; 2,3,9,10,16,17,23,24-octakis(3,6-dioxaheptyloxy) phthalocyanine; octa-n-butoxy phthalocyanine; phthalocyanine; phthalocyanine sulfonate; phthalocyanine tetrasulphonate; phthalocyanine tetrasulfonate; t-butyl-phthalocyanine; tetra-t-butyl phthalocyanine; and tetradibenzobarreleno-octabutoxy-phthalocyanine.

Exemplary porphycenes include 2,3-($2^3$-carboxy-$2^4$-methoxycarbonyl benzo)-7,12,17-tris(2-methoxyethyl) porphycene; 2-(2-hydroxyethyl)-7,12,17-tri(2-methoxyethyl) porphycene; 2-(2-hydroxyethyl)-7,12,17-tri-n-propyl-porphycene; 2-(2-methoxyethyl)-7,12,17-tri-n-propyl-porphycene; 2,7,12,17-tetrakis(2-methoxyethyl) porphycene; 2,7,12,17-tetrakis(2-methoxyethyl)-9-hydroxy-porphycene; 2,7,12,17-tetrakis(2-methoxyethyl)-9-methoxy-porphycene; 2,7,12,17-tetrakis(2-methoxyethyl)-9-n-hexyloxy-porphycene; 2,7,12,17-tetrakis(2-methoxyethyl)-9-acetoxy-porphycene; 2,7,12,17-tetrakis(2-methoxyethyl)-9-caproyloxy-porphycene; 2,7,12,17-tetrakis (2-methoxyethyl)-9-pelargonyloxy-porphycene; 2,7,12,17-tetrakis(2-methoxyethyl)-9-stearoyloxy-porphycene; 2,7,12,17-tetrakis(2-methoxyethyl)-9-(N-t-butoxycarbonylglycinoxy) porphycene; 2,7,12,17-tetrakis (2-methoxyethyl)-9-[4-((β-apo-7-carotenyl)benzoyloxyl-porphycene; 2,7,12,17-tetrakis(2-methoxyethyl)-9-amino-porphycene; 2,7,12,17-tetrakis($^2$-methoxyethyl)-9-acetamido-porphycene; 2,7,12,17-tetrakis(2-methoxyethyl)-9-glutaramido-porphycene; 2,7,12,17-tetrakis(2-methoxyethyl)-9-(methyl-glutaramido)-porphycene; 2,7,12,17-tetrakis(2-methoxyethyl)-9-(glutarimido)-porphycene; 2,7,12,17-tetrakis(2-methoxyethyl)-3-(N,N-dimethylaminomethyl)-porphycene; 2,7,12,17-tetrakis(2-methoxyethyl)-3-(N,N-dimethylaminomethyl)-porphycene hydrochloride; 2,7,12,17-tetrakis(2-ethoxyethyl)-porphycene; 2,7,12,17-tetra-n-propyl-porphycene; 2,7,12,17-tetra-n-propyl-9-hydroxy-porphycene; 2,7,12,17-tetra-n-propyl-9-methoxy-porphycene; 2,7,12,17-tetra-n-propyl-9-acetoxy porphycene; 2,7,12,17-tetra-n-propyl-9-(t-butyl glutaroxy)-porphycene; 2,7,12,17-tetra-n-propyl-9-(N-t-butoxycarbonylglycinoxy)-porphycene; 2,7,12,17-tetra-n-propyl-9-(4-N-t-butoxy-carbonyl-butyroxy)-porphycene; 2,7,12,17-tetra-n-propyl-9-amino-porphycene; 2,7,12,17-tetra-n-propyl-9-acetamido-porphycene; 2,7,12,17-tetra-n-propyl-9-glutaramido-porphycene; 2,7,12,17-tetra-n-propyl-9-(methyl glutaramido)-porphycene; 2,7,12,17-tetra-n-propyl-3-(N,N-dimethylaminomethyl) porphycene; 2,7,12,17-tetra-n-propyl-9,10-benzo porphycene; 2,7,12,17-tetra-n-propyl-9-p-benzoyl carboxy-porphycene; 2,7,12,17-tetra-n-propyl-porphycene; 2,7,12,17-tetra-t-butyl-3,6;13,16-dibenzo-porphycene; 2,7-bis(2-hydroxyethyl)-12,17-di-n-propyl-porphycene; 2,7-bis(2-methoxyethyl)-12,17-di-n-propyl-porphycene; and porphycene.

Exemplary porphyrins include 5-azaprotoporphyrin dimethylester; bis-porphyrin; coproporphyrin III; coproporphyrin III tetramethylester; deuteroporphyrin; deuteroporphyrin IX dimethylester; diformyldeuteroporphyrin IX dimethylester; dodecaphenylporphyrin; hematoporphyrin; hematoporphyrin (8 μM); hematoporphyrin (400 μM); hematoporphyrin (3 μM); hematoporphyrin (18 μM); hematoporphyrin (30 μM); hematoporphyrin (67 μM); hematoporphyrin (150 μM); hematoporphyrin IX; hematoporphyrin monomer; hematoporphyrin dimer; hematoporphyrin derivative; hematoporphyrin derivative (6 μM); hematoporphyrin derivative (200 μM); hematoporphyrin derivative A (20 μM); hematoporphyrin IX dihydrochloride; hematoporphyrin dihydrochloride; hematoporphyrin IX dimethylester; haematoporphyrin IX dimethylester; mesoporphyrin dimethylester; mesoporphyrin IX dimethylester; monoformyl-monovinyl-deuteroporphyrin IX dimethylester; monohydroxyethylvinyl deuteroporphyrin; 5,10,15,20-tetra(o-hydroxyphenyl) porphyrin; 5,10,15,20-tetra(m-hydroxyphenyl) porphyrin; 5,10,15,20-tetrakis-(m-hydroxyphenyl) porphyrin; 5,10,15,20-tetra(p-hydroxyphenyl) porphyrin; 5,10,15,20-tetrakis (3-methoxyphenyl) porphyrin; 5,10,15,20-tetrakis (3,4-dimethoxyphenyl) porphyrin; 5,10,15,20-tetrakis (3,5-dimethoxyphenyl) porphyrin; 5,10,15,20-tetrakis (3,4,5-trimethoxyphenyl) porphyrin; 2,3,7,8,12,13,17,18-octaethyl-5,10,15,20-tetraphenylporphyrin; Photofrin®; Photofrin® II; porphyrin c; protoporphyrin; protoporphyrin IX; protoporphyrin dimethylester; protoporphyrin IX dimethylester; protoporphyrin propylaminoethylformamide iodide; protoporphyrin N,N-dimethylaminopropylformamide; protoporphyrin propylaminopropylformamide iodide; protoporphyrin butylformamide; protoporphyrin N,N-dimethylamino-formamide; protoporphyrin formamide; sapphyrin 13,12,13,22-tetraethyl-2,7,18,23 tetramethyl sapphyrin-8,17-dipropanol; sapphyrin 23,12,13,22-tetraethyl-2,7,18,23 tetramethyl sapphyrin-8-monoglycoside; sapphyrin 3; meso-tetra-(4-N-carboxyphenyl)-porphine; tetra-(3-methoxyphenyl)-porphine; tetra-(3-methoxy-2,4-difluorophenyl)-porphine; 5,10,15,20-tetrakis(4-N-methylpyridyl) porphine; meso-tetra -(4-N-methylpyridyl)-porphine tetrachloride; meso-tetra(4-N-methylpyridyl)-porphine; meso-tetra-(3-N-methylpyridyl)-porphine; meso-tetra-(2-N-methylpyridyl)-porphine; tetra(4-N,N,N-trimethylanilinium) porphine; meso-tetra-(4-N,N,N"-trimethylamino-phenyl) porphine tetrachloride; tetranaphthaloporphyrin; 5,10,15,20-tetraphenylporphyrin; tetraphenylporphyrin; meso-tetra-(4-N-sulfonatophenyl)-porphine; tetraphenylporphine tetrasulfonate; meso-tetra(4-sulfonatophenyl)porphine; tetra (4-sulfonatophenyl)porphine; tetraphenylporphyrin sulfonate; meso-tetra(4-sulfonatophenyl)porphine; tetrakis (4-sulfonatophenyl)porphyrin; meso-tetra(4-sulfonatophenyl)porphine; meso(4-sulfonatophenyl) porphine; meso-tetra(4-sulfonatophenyl)porphine; tetrakis (4-sulfonatophenyl)porphyrin; meso-tetra(4-N-trimethylanilinium)-porphine; uroporphyrin; uroporphyrin I (17 $\mu$M); uroporphyrin IX; and uroporphyrin I (18 $\mu$M).

Exemplary psoralens include psoralen; 5-methoxypsoralen; 8-methoxypsoralen; 5,8-dimethoxypsoralen; 3-carbethoxypsoralen; 3-carbethoxy-pseudopsoralen; 8-hydroxypsoralen; pseudopsoralen; 4,5',8-trimethylpsoralen; allopsoralen; 3-aceto-allopsoralen; 4,7-dimethyl-allopsoralen; 4,7,4'-trimethyl-allopsoralen; 4,7,5'-trimethyl-allopsoralen; isopseudopsoralen; 3-acetoisopseudopsoralen; 4,5'-dimethyl-isopseudopsoralen; 5',7-dimethyl-isopseudopsoralen; pseudoisopsoralen; 3-acetopseudoisopsoralen; 3/4',5'-trimethyl-aza-psoralen; 4,4',8-trimethyl-5'-amino-methylpsoralen; 4,4',8-trimethyl-phthalamyl-psoralen; 4,5',8-trimethyl-4'-aminomethyl psoralen; 4,5',8-trimethyl-bromopsoralen; 5-nitro-8-methoxy-psoralen; 5'-acetyl-4,8-dimethyl-psoralen; 5'-aceto-8-methyl-psoralen; and 5'-aceto-4,8-dimethyl-psoralen.

Exemplary purpurins include octaethylpurpurin; octaethylpurpurin zinc; oxidized octaethylpurpurin; reduced octaethylpurpurin; reduced octaethylpurpurin tin; purpurin 18; purpurin-18; purpurin-18-methyl ester; purpurin; tin ethyl etiopurpurin I; Zn(II) aetio-purpurin ethyl ester; and zinc etiopurpurin.

Exemplary quinones include 1-amino-4,5-dimethoxy anthraquinone; 1,5-diamino-4,8-dimethoxy anthraquinone; 1,8-diamino-4,5-dimethoxy anthraquinone; 2,5-diamino-1,8-dihydroxy anthraquinone; 2,7-diamino-1,8-dihydroxy anthraquinone; 4,5-diamino-1,8-dihydroxy anthraquinone; mono-methylated 4,5- or 2,7-diamino-1,8-dihydroxy anthraquinone; anthralin (keto form); anthralin; anthralin anion; 1,8-dihydroxy anthraquinone; 1,8-dihydroxy anthraquinone (Chrysazin); 1,2-dihydroxy anthraquinone; 1,2-dihydroxy anthraquinone (Alizarin); 1,4-dihydroxy anthraquinone (Quinizarin); 2,6-dihydroxy anthraquinone; 2,6-dihydroxy anthraquinone (Anthraflavin); 1-hydroxy anthraquinone (Erythroxy-anthraquinone); 2-hydroxy-anthraquinone; 1,2,5,8-tetra-hydroxy anthraquinone (Quinalizarin); 3-methyl-1,6,8-trihydroxy anthraquinone (Emodin); anthraquinone; anthraquinone-2-sulfonic acid; benzoquinone; tetramethyl benzoquinone; hydroquinone; chlorohydroquinone; resorcinol; and 4-chlororesorcinol.

Exemplary retinoids include all-trans retinal; $C_{17}$ aldehyde; $C_{22}$ aldehyde; 11-cis retinal; 13-cis retinal; retinal; and retinal palmitate.

Exemplary rhodamines include 4,5-dibromo-rhodamine methyl ester; 4,5-dibromo-rhodamine n-butyl ester; rhodamine 101 methyl ester; rhodamine 123; rhodamine 6G; rhodamine 6G hexyl ester; tetrabromo-rhodamine 123; and tetramethyl-rhodamine ethyl ester.

Exemplary thiophenes include terthiophenes such as 2,2':5',2"-terthiophene; 2,2':5',2"-terthiophene-5-carboxamide; 2,2':5',2"-terthiophene-5-carboxylic acid; 2,2':5',2"-terthiophene-5-L-serine ethyl ester; 2,2':5',2"-terthiophene-5-N-isopropynyl-formamide; 5-acetoxymethyl-2,2':5',2"-terthiophene; 5-benzyl-2,2':5',2"-terthiophene-sulphide; 5-benzyl-2,2':5',2"-terthiophene-sulfoxide; 5-benzyl-2,2':5',2"-terthiophene-sulphone; 5-bromo-2,2':5',2"-terthiophene; 5-(butynyl-3'"-hydroxy)-2,2':5',2"-terthiophene; 5-carboxyl-5"-trimethylsilyl-2,2':5',2"-terthiophene; 5-cyano-2,2':5',2"-terthiophene; 5,5"-dibromo-2,2':5',2"-terthiophene; 5-(1'",1'"-dibromoethenyl)-2,2':5',2"-terthiophene; 5,5"-dicyano-2,2':5',2"-terthiophene; 5,5"-diformyl-2,2':5',2"-terthiophene; 5-difluoromethyl-2,2':5',2"-terthiophene; 5,5"-diiodo-2,2':5',2"-terthiophene; 3,3"-dimethyl-2,2':5',2"-terthiophene; 5,5"-dimethyl-2,2':5',3,3"-dimethyl-2,2':5',2"-terthiophene; 5,5"-dimethyl-2,2':5',2"-terthiophene; 5-(3'",3'"-dimethylacryloyloxymethyl)-2,2':5',2"-terthiophene; 5,5"-di-(t-butyl)-2,2':5',2"-terthiophene; 5,5"-dithiomethyl-2,2':5',2"-terthiophene; 3'-ethoxy-2,2':5',2"-terthiophene; ethyl 2,2':5',2"-terthiophene-5-carboxylic acid; 5-formyl-2,2':5',2"-terthiophene; 5-hydroxyethyl-2,2':5',2"-terthiophene; 5-hydroxymethyl-2,2':5',2"-terthiophene; 5-iodo-2,2':5',2"-terthiophene; 5-methoxy-2,2':5',2"-terthiophene; 3'-methoxy-2,2':5',2"-terthiophene; 5-methyl-2,2':5',2"-terthiophene; 5-(3'"-methyl-2'"-butenyl)-2,2':5',2"-terthiophene; methyl 2,2':5',2"-terthiophene-5-[3'"-acrylate]; methyl 2,2':5',2"-terthiophene-5-(3'"-propionate); N-allyl-2,2':5',2"-terthiophene-5-sulphonamide; N-benzyl-2,2':5',2"-terthiophene-5-sulphonamide; N-butyl-2,2':5',2"-terthiophene-5-sulphonamide; N,N-diethyl-2,2':5',2"-terthiophene-5-sulphonamide; 3,3',4',3"-tetramethyl-2,2':5',2"-terthiophene; 5-t-butyl-5"-trimethylsilyl -2,2':5',2"-terthiophene; 3'-thiomethyl-2,2':5',2"-terthiophene; 5-thiomethyl-2,2':5',2"-terthiophene; 5-trimethylsilyl-2,2':5',2"-terthiophene, bithiophenes such as 2,2'-bithiophene; 5-cyano-2,2'-bithiophene; 5-formyl-2,2'-bithiophene; 5-phenyl-2,2'-bithiophene; 5-(propynyl)-2,2'-bithiophene; 5-(hexynyl)-2,2'-bithiophene; 5-(octynyl)-2,2'-bithiophene; 5-(butynyl-4"-hydroxy)-2,2'-bithiophene; 5-(pentynyl-5"-hydroxy)-2,2'-bithiophene; 5-(3",4"-dihydroxybutynyl)-2,2'-bithiophene derivative; 5-(ethoxybutynyl)-2,2'-bithiophene derivative, and misclaneous thiophenes such as 2,5-diphenylthiophene; 2,5-di(2-thienyl)furan; pyridine,2,6-bis(2-thienyl)-; pyridine, 2,6-bis(thienyl)-; thiophene, 2-(1-naphthalenyl)-; thiophene, 2-(2-naphthalenyl)-; thiophene, 2,2'-(1,2-phenylene)bis-; thiophene, 2,2'-(1,3-phenylene) bis-; thiophene, 2,2'-(1,4-phenylene)bis-; 2,2':5',2":5",2'"-quaterthiophene; α-quaterthienyl; α-tetrathiophene; α-pentathiophene; α-hexathiophene; and α-heptathiophene.

Exemplary verdins include copro (II) verdin trimethyl ester; deuteroverdin methyl ester; mesoverdin methyl ester; and zinc methyl pyroverdin.

Exemplary vitamins include ergosterol (provitamin D2); hexamethyl-Co a Co b-dicyano-7-de(carboxymethyl)-7,8-didehydro-cobyrinate (Pyrocobester); pyrocobester; and vitamin D3.

Exemplary xanthene dyes include Eosin B (4',5'-dibromo, 2',7'-dinitro-fluorescein, dianion); eosin Y; eosin Y (2',4',5',7'-tetrabromo-fluorescein, dianion); eosin (2',4',5',7'-tetrabromo-fluorescein, dianion); eosin (2',4',5',7'-tetrabromo-fluorescein, dianion) methyl ester; eosin (2',4', 5',7'-tetrabromo-fluorescein, monoanion) p-isopropylbenzyl ester; eosin derivative (2',7'-dibromo-fluorescein, dianion); eosin derivative (4',5'-dibromo-fluorescein, dianion); eosin derivative (2',7'-dichloro-fluorescein, dianion); eosin derivative (4',5'-dichloro-fluorescein, dianion); eosin derivative (2',7'-diiodo-fluorescein, dianion); eosin derivative (4',5'-diiodo-fluorescein, dianion); eosin derivative (tribromo-fluorescein, dianion); eosin derivative (2',4',5',7'-tetrachloro-fluorescein, dianion); eosin; eosin dicetylpyridinium chloride ion pair; erythrosin B (2',4',5',7'-tetraiodo-fluorescein, dianion); erythrosin; erythrosin dianion; erythrosin B; fluorescein; fluorescein dianion; phloxin B (2',4',5',7'-tetrabromo-3,4,5,6-tetrachloro-fluorescein, dianion); phloxin B (tetrachloro-tetrabromo-fluorescein); phloxine B; rose bengal (3,4,5,6-tetrachloro-2',4',5',7'-tetraiodofluorescein, dianion); rose bengal; rose bengal dianion; rose bengal O-methyl-methylester; rose bengal 6'-O-acetyl ethyl ester; rose bengal benzyl ester diphenyl-diiodonium salt; rose bengal benzyl ester triethylammonium salt; rose bengal benzyl ester, 2,4,6,-triphenylpyrilium salt; rose bengal benzyl ester, benzyltriphenyl-phosphonium salt; rose bengal benzyl ester, benzyltriphenyl phosphonium salt; rose bengal benzyl ester, diphenyl-iodonium salt; rose bengal benzyl ester, diphenyl-methylsulfonium salt; rose bengal benzyl ester, diphenyl-methyl-sulfonium salt; rose bengal benzyl ester, triethyl-ammonium salt; rose bengal benzyl ester, triphenyl pyrilium; rose bengal bis (triethyl-ammonium) salt) (3,4,5,6-tetrachloro-2',4',5',7'-tetraiodofluorescein, bis (triethyl-ammonium salt); rose bengal bis (triethyl-ammonium) salt; rose bengal bis(benzyl-triphenyl-phosphonium) salt (3,4,5,6-tetrachloro-2',4',5',7'-tetraiodofluorescein, bis(benzyl-triphenyl-phosphonium) salt); rose bengal bis(diphenyl-iodonium) salt (3,4,5,6-tetrachloro-2',4',5',7'-tetraiodofluorescein, bis(diphenyl-iodonium) salt); rose bengal di-cetyl-pyridinium chloride ion pair; rose bengal ethyl ester triethyl ammonium salt; rose bengal ethyl ester triethyl ammonium salt; rose bengal ethyl ester; rose bengal methyl ester; rose bengal octyl ester tri-n-butyl-ammonium salt RB; rose bengal, 6'-O-acetyl-, and ethyl ester.

Particularly preferred PSs are the green porphyrins, such as BPD-DA, -DB, -MA, and -MB, and in particular BPD-MA, EA6, and B3. These compounds are porphyrin derivatives obtained by reacting a porphyrin nucleus with an alkyne in a Diels-Alder type reaction to obtain a monohydrobenzoporphyrin, and they are described in detail in the issued U.S. Pat. No. 5,171,749, which is hereby incorporated in its entirety by reference. Other photosensitizers that may be used in the present invention include those described in U.S. Pat. Nos. 5,308,608, 6,093,739, 5,703,230, 5,831,088, 5,726,304, and 5,405,957. Of course, combinations of photosensitizers may also be used. It is preferred that the absorption spectrum of the photosensitizer be in the visible range, typically between 350 nm and 1200 nm, more preferably between 400–900 nm, and even more preferably between 600–900 nm.

BPD-MA is described, for example, in U.S. Pat. No. 5,171,749; EA6 and B3 are described in U.S. Ser. Nos. 09/088,524 and 08/918,840, respectively, all of which are incorporated herein by reference. Preferred green porphyrins have the basic structure:

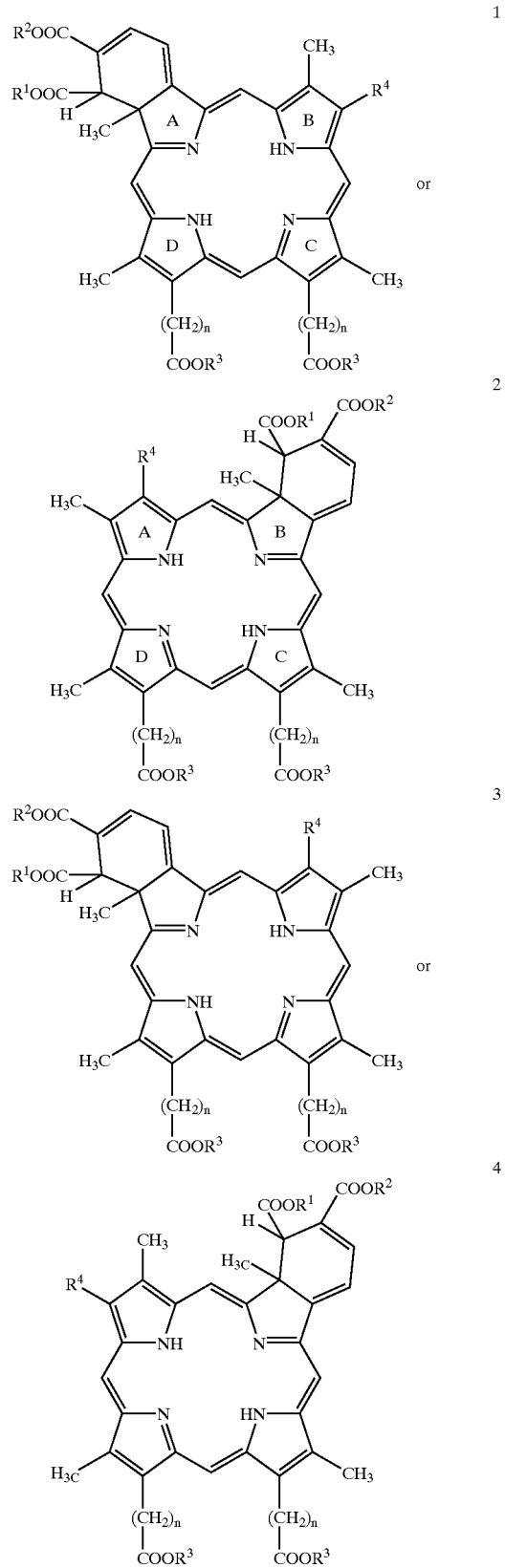

where $R^4$ is vinyl or 1-hydroxyethyl and $R^1$, $R^2$, and $R^3$ are H or alkyl or substituted alkyl.

BPD-MA has the structure shown in formula 1 wherein $R^1$ and $R^2$ are methyl, $R^4$ is vinyl and one of $R^3$ is H and the other is methyl. EA6 is of formula 2 wherein $R^1$ and $R^2$ are methyl and both $R^3$ are 2-hydroxyethyl (i.e., the ethylene glycol esters). B3 is of formula 2 wherein $R^1$ is methyl, $R^2$ is H, and both $R^3$ are methyl. In both EA6 and B3, $R^4$ is also vinyl.

The representations of BPD-MAC and BPD-MAD, which are the components of Verteporfin, as well as illustrations of A and B ring forms of EA6 and B3, are as follows:

BPD-MA$_C$

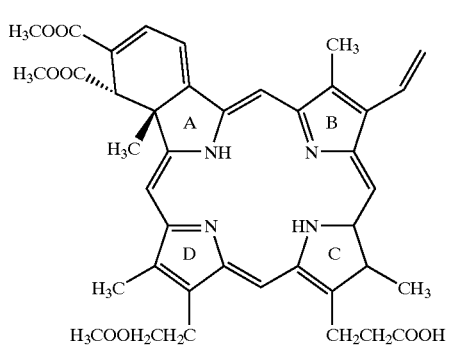

BPD-MA$_D$

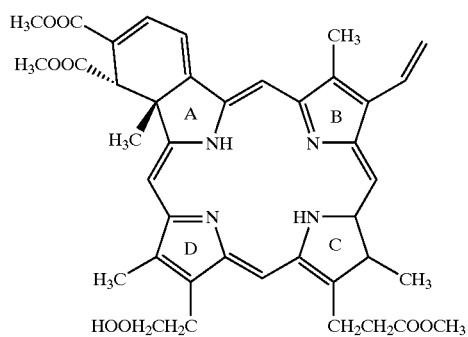

A-EA6

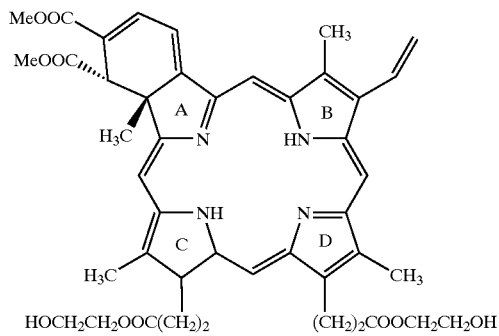

B-EA6

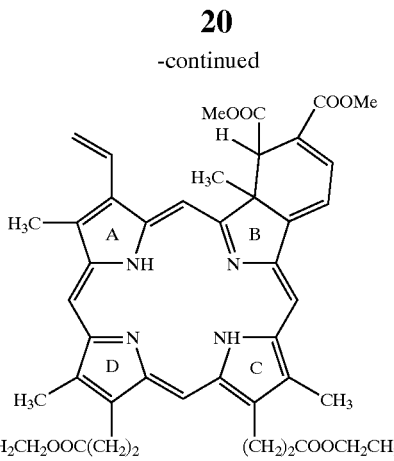

A-B3

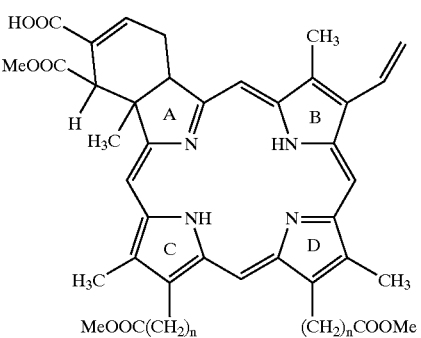

B-B3

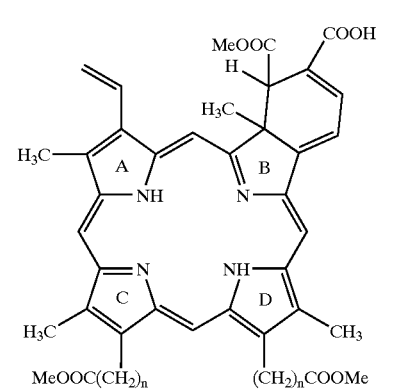

Related compounds of formulas 3 and 4 are also useful; in general, $R^4$ will be vinyl or 1-hydroxyethyl and $R^1$, $R^2$, and $R^3$ are H or alkyl or substituted alkyl.

As disclosed herein, reduced fluence rates are preferred for the practice of the invention. Reduced fluence rates should not be confused with total PDT dose, which is generally described as the combination of the concentration of the photosensitizing drug, the intensity of the radiation employed and the time of exposure to light, which determines the total amount of energy ultimately delivered to the target tissue. The fluence rate is but one part of the total PDT dose and as such may be changed with or without affecting the total PDT dose depending on the time of light exposure. For example, if the fluence rate is reduced and the time kept constant, a lower total PDT dose is provided. Alternatively, if the fluence rate is reduced and the time of exposure increased, the same total PDT dose can be provided. Reduced fluence rates have the additional advantage of decreasing the likelihood of hyperthermic and other damaging effects.

Reduced fluence rates have been considered in the context of PDT treatment of tumors as the target tissue. See Henderson et al. (*Cancer Res.* 47:3110–3114 (1987)), Tromberg et al. (*Photochem. and Photobiol.* 52(2):375–385 (1990)), Sitnik et al. (*Photochem. and Photobiol.* 67(4):462–466 (1998)), Sitnik et al. (*British J. Cancer* 77(9):1.86-1394 (1998)), and Henderson et al. (*Cancer Res.* 60:525–529 (2000)). While these studies are of interest because of the reduced oxygen levels (hypoxic conditions) seen in tumors due to inadequate vascularization, they do not relate to the present invention where neovascularization per se is the target tissue.

It is understood that the selection of particular fluence rates will vary according to the nature of the neovasculature and tissue being treated and the nature of the PS employed. However, the conditions for PDT (including PS concentration, fluence rate, and time of irradiation) cannot vary over any arbitrary range. There are actual constraints which are known by the skilled practitioner with the use of any PS in PDT. Preferred rates for use with green porphyrins or BPDs is from about 200 to 250, about 250 to 300, about 300 to 350, about 350 to 400, about 400 to 450, about 450 to 500, and about 500 to 550 mW/cm$^2$. Particularly preferred is a fluence rate of 300 mW/cm$^2$.

As indicated above, the total PDT dose depends on the balance of at least the concentration of PS employed, light intensity (fluence rate), and time of irradiation which determines total energy. The values set forth hereinbelow for these parameters indicates the range in which they may be varied; however, equivalents of the following are known to the skilled practitioner and are also within the scope of the invention.

The PS concentration in the formulation to be administered will depend on the nature of the tissue to be treated, the manner in which the formulation is administered, and the nature of the PS. Typical concentrations, however, are in the range of about 1 ng/ml to about 10 µg/ml, preferably about 2 ng/ml to about 1 µg/ml, and typically in the range of about 10 ng/ml to about 100 ng/ml. However, these values are merely suggestions and may not apply to all PSs. For localized application of BPD-MA and other green porphyrins or porphyrin derivatives (especially those listed above), a range of about 0.01 to about 0.2 or about 0.5 mg/ml is contemplated. Preferably, about 0.075 mg/ml is used. For systemic application of PS, the range may be about 2–8 (or more preferably 6) mg/m$^2$ (BPD-MA/body surface area). 6 mg/m$^2$ is approximately 0.15 mg/kg.

Systemic administration can also be stated in terms of amount of PS to body weight of the subject being treated. Dosages for this invention stated in such terms are less than about 10 µg/kg to 100 mg/kg body weight, preferably less than about 10 mg/kg, more preferably about 0.15 mg/kg in humans. Preferably, the PS is infused into a subject over a short period, such as, but not limited to, about 5 to about 120 minutes, about 10 to about 90 minutes, about 20 to about 60 minutes, or about 30 to 45 minutes. Particularly preferred is an infusion over 10 minutes.

In applications of the present invention to the treatment of ocular neovasculature (such as that of the cornea, iris, retina), the photoactive agent is preferably formulated so as to deliver an effective concentration to the target ocular tissue. The photoactive agent may be coupled to a specific binding ligand which may bind to a specific surface component of the target ocular tissue or, if desired, by formulation with a carrier that delivers higher concentrations to the target tissue. The formulation may be a liposomal formulation, an emulsion, or simply an aqueous solution. Buffers and other excipients may also be added. Gelling agents and other excipients may also be employed.

The nature of the formulation will depend in part on the mode of administration and on the nature of the photoactive agent selected. To prepare a pharmaceutical formulation or composition comprising a PS of the invention, any pharmaceutically acceptable excipient, or combination thereof, appropriate to the particular photoactive compound may be used. Thus, the photoactive compound may be administered as an aqueous composition, as a transmucosal or transdermal composition, or in an oral formulation. Liposomal compositions are particularly preferred especially where the photoactive agent is a green porphyrin. Liposomal formulations are believed to deliver the green porphyrin selectively to the low-density lipoprotein component of plasma which, in turn acts as a carrier to deliver the active ingredient more effectively to the desired site. Increased numbers of LDL receptors have been shown to be associated with neovascularization, and by increasing the partitioning of the green porphyrin into the lipoprotein phase of the blood, it appears to be delivered more efficiently to neovasculature.

The optimum time following PS administration until light treatment can also vary widely depending on the mode of administration, the form of administration and the specific ocular tissue being targeted. Typical times after administration of the photoactive agent range from about 1 minute to about 2 hours, preferably about 5–30 minutes, and more preferably about 10–25 minutes. Particularly preferred is irradiation at 15 minutes after the start of PS infusion. The incubation before irradiation may occur in the dark or low-level light may be supplied during PS administration.

The irradiation levels will be in the range generally employed for PDT treatment of CNV as known in the art. Typical levels for the practice of the invention are in the range of about 12.5, 25, 50, 75, and 100 J/cm$^2$. Preferred are fluence rates of about 300 mW/cm$^2$ used to deliver about 25 J/cm$^2$ in about 83 seconds, about 12.5 J/cm$^2$ in about 42 seconds, and about 50 J/cm$^2$ in about 166 seconds. The radiation can be supplied by any convenient source using a wavelength absorbed by the PS used. Examples of sources for use in the present methods include any assembly capable of producing visible light.

PS spectra, as well as wavelengths for PS activation, have been described in the art. Irradiation of the administered PS is preferably at the wavelength absorbed by the PS selected. For any particular PS, it is a trivial matter to ascertain the spectrum. For green porphyrins, however, the desired wavelength range is generally between about 550 and 695 nm. Preferred wavelengths for the practice of the invention are at about 685–695 nm, particularly at about 686, about 687, about 688, about 689, about 690, about 691, and about 692 nm.

Treatments in accordance with the present invention can be repeated. For example, and without limiting the invention, treatments may be repeated at approximately three month intervals (+/−2 weeks) if CNV leakage is found to continue or as deemed necessary by the skilled practitioner.

Treatment efficacy can be evaluated by a number of different protocols, including, but not limited to fluorescein angiography to determine the area of CNV leakage. Closure of choroidal neovascularization may also be confirmed histologically by the observation of damage to endothelial cells. Observations to detect vacuolated cytoplasm and abnormal nuclei associated with disruption of neovascular tissue may also be evaluated.

Of particular importance with respect to the present invention is the evaluation of visual acuity. This is done using means standard in the art and conventional "eye charts" in which visual acuity is evaluated by the ability to discern letters of a certain size, usually with five letters on a line of given size. Measures of visual acuity are known in the art and standard means are used to evaluate visual acuity according to the present invention.

The following examples are intended to illustrate but not to limit the invention.

EXAMPLE 1

Materials and Methods

Subjects will receive either VISUDYNE™ (verteporfin for injection) delivered as a two-step process: 1) a 10-minute intravenous infusion of VISUDYNE™ (6 mg/m$^2$) and 2) light application 15 minutes after the start of the infusion using a light dose of 50 J/cm2 (600 mW/cm$^2$) or 25 J/cm$^2$ (300 mW/cm$^2$).

Retreatment may be administered at 3-month intervals (±2 weeks) through Month 9, if evidence of CNV leakage is detected by fluorescein angiography. Subjects who have a severe vision decrease of vision of ≧20 letters within 7 days of treatment should not be retreated unless their vision completely returns to pretreatment levels.

Each vial of VISUDYNE™ will be reconstituted with 7 mL of Sterile Water for injection to provide 7.5 mL containing a final concentration of 2 mg/mL. Reconstituted VISUDYNE™ is protected from light and used within 4 hours. Reconstituted VISUDYNE™ is an opaque dark green solution.

The volume of reconstituted VISUDYNE™ required to achieve the desired dose of 6 mg/m2 body surface area is withdrawn from the vial and diluted with 5% Dextrose for Injection to a total infusion volume of 30 mL. The full infusion volume is administered intravenously over 10 minutes at a rate of 3 mL/minute, using an appropriate syringe pump and in-line filter.

Light application to the eye will be performed 15 minutes after the start of infusion of VISUDYNE™. The light dose of 25 or 50 J/cm$^2$ is delivered over 83 seconds at a light fluence rate of either 300 or 600 mW/cm$^2$, respectively. Red light (689±3 nm) produced by a diode laser will be delivered to the CNV lesion as a single circular spot through a fiber optic and a slit lamp using a suitable contact lens. Light delivery from the diode laser will stop automatically after the preset light dose is delivered.

The size of the CNV lesion is estimated from the fluorescein angiograms that delineate the classic and occult CNV and any features that block the boundaries of any classic or occult CNV. The greatest linear dimension (GLD) of the lesion on the retina is determined from the fluorescein angiogram using a reticule with a straight-line scale of 20 mm subdivided into 200 units. The GLD of the lesion on the angiogram is divided by the magnification factor for the fundus camera, to give the actual diameter of the light spot on the retina. One thousand microns is then added to the GLD to allow a 500 micron border to ensure full coverage of the lesion. This gives the desired diameter of the light spot size.

The reticule can also be used to gauge where the light spot will land on the retina (and retinal landmarks). The light spot covering the lesion must come no closer than 200 microns to the optic disc. If the lesion or proposed treatment extends closer to the optic disc than 200 microns, it is appropriate to leave this portion of the CNV lesion untreated.

EXAMPLE 2

Reduced Fluence Protocol

Subjects with minimally classic subfoveal CNV (a subtype of CNV) secondary to AMD will be treated with each of the protocols as shown below.
1. VISUDYNE therapy using a reduced light fluence rate of 300 mW/cm$^2$,
2. VISUDYNE therapy using the standard light fluence rate of 600 mW/cm$^2$, At Week 1, fluorescein and ICG angiographic assessments will be evaluated compared to baseline for the first 10 evaluable subjects in each treatment group. Fluorescein angiography will be used to determine the area of CNV leakage. The Week 1 comparison will be conducted to look for a non-effect of the reduced light fluence rate group. The number of subjects with classic CNV leakage in the reduced light fluence (300 mW/cm$^2$) group and the standard light fluence (600 mW/cm$^2$) group will be compared at 1 week.

Fluorescein and ICG angiographic assessments will be performed at Week 6.

All patients will continue follow-up visits until the last subject has completed his/her Month 3 visit. At this time, the angiographic outcomes and median visual acuity change from baseline will be evaluated for these subjects.

All references cited herein are hereby incorporated by reference in their entireties, whether previously specifically incorporated or not. As used herein, the terms "a", "an", and "any" are each intended to include both the singular and plural forms.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method for effecting the closure of choroidal neovasculature in a human subject using photodynamic therapy (PDT), said method comprising
   administering a photosensitizer (PS) to said subject afflicted with said neovasculature, and
   irradiating the PS with electromagnetic radiation containing a wavelength absorbed by said PS at a reduced fluence rate which does not deplete molecular oxygen levels in said neovasculature,
   wherein the fluence rate delivers a total light dose ranging from about 12.5 to about 25 J/cm$^2$,
   wherein closure of choroidal neovasculature in said subject is effected.

2. The method of claim 1, wherein the choroidal neovasculature (CNV) is in a subject afflicted or diagnosed with age-related macular degeneration (AMD).

3. The method of claim 2, wherein the AMD is the "wet" form.

4. The method of claim 1, wherein the PS is administered as a pharmaceutical composition.

5. The method of claim 1, wherein the PS is administered at a concentration ranging between about 2 to 8 mg/m$^2$ (PS/body surface area of subject).

6. The method of claim 5, wherein the PS is administered at a concentration of 6 mg/m$^2$.

7. The method of claim 1, wherein the PS is administered at a concentration ranging between about 10 μg/kg to 100 mg/kg (PS/body weight of subject).

8. The method of claim 7, wherein the green porphyrin is selected from BPD-DA, BPD-DB, BPD-MA, BPD-MB, EA6, and B3.

9. The method of claim 7, wherein the PS is coupled to a specific binding ligand.

10. The method of claim 9, wherein the formulation is selected from the group consisting of a liposome, emulsion, or aqueous solution.

11. The method of claim 10, wherein the reduced fluence rate is 300 or about 300 mW/cm$^2$.

12. The method of claim 1, wherein the PS is a green porphyrin.

13. The method of claim 12, wherein the green porphyrin is BPD-MA.

14. The method of claim 1, wherein the PS is formulated with a carrier.

15. The method of claim 1, wherein the reduced fluence rate is between about 200 mW/cm$^2$ and about 500 mW/cm$^2$.

16. The method of claim 1, wherein the electromagnetic radiation contains wavelengths in the visible light spectra.

17. The method of claim 1, wherein said irradiating occurs between 5 to 30 minutes after administration.

18. A method of effecting the closure of choroidal neovasculature in a human subject, said method comprising
irradiating said subject afflicted with said neovasculature, and to whom a photosensitizer (PS) has been administered, with electromagnetic radiation containing a wavelength absorbed by said PS at a reduced fluence rate which permits the continued production of singlet oxygen,
wherein the fluence rate delivers a total light dose ranging from about 12.5 to about 25 J/cm$^2$,
wherein closure of choroidal neovasculature in said subject is effected.

19. A method of preventing depletion of molecular oxygen while closing neovasculature during photodynamic therapy (PDT) comprising irradiation with photosensitizer activating radiation at a reduced fluence rate of less than 550 mW/cm$^2$, wherein the fluence rate delivers a total light dose ranging from about 12.5 to about 25 J/cm$^2$.

20. The method of claim 1, wherein the reduced fluence rate is less than about 500 mW/cm$^2$.

* * * * *